Nov. 26, 1974 W. H. JESSEL, JR., ET AL Plant Pat. 3,657
CHRYSANTHEMUM PLANT
Filed Oct. 10, 1973
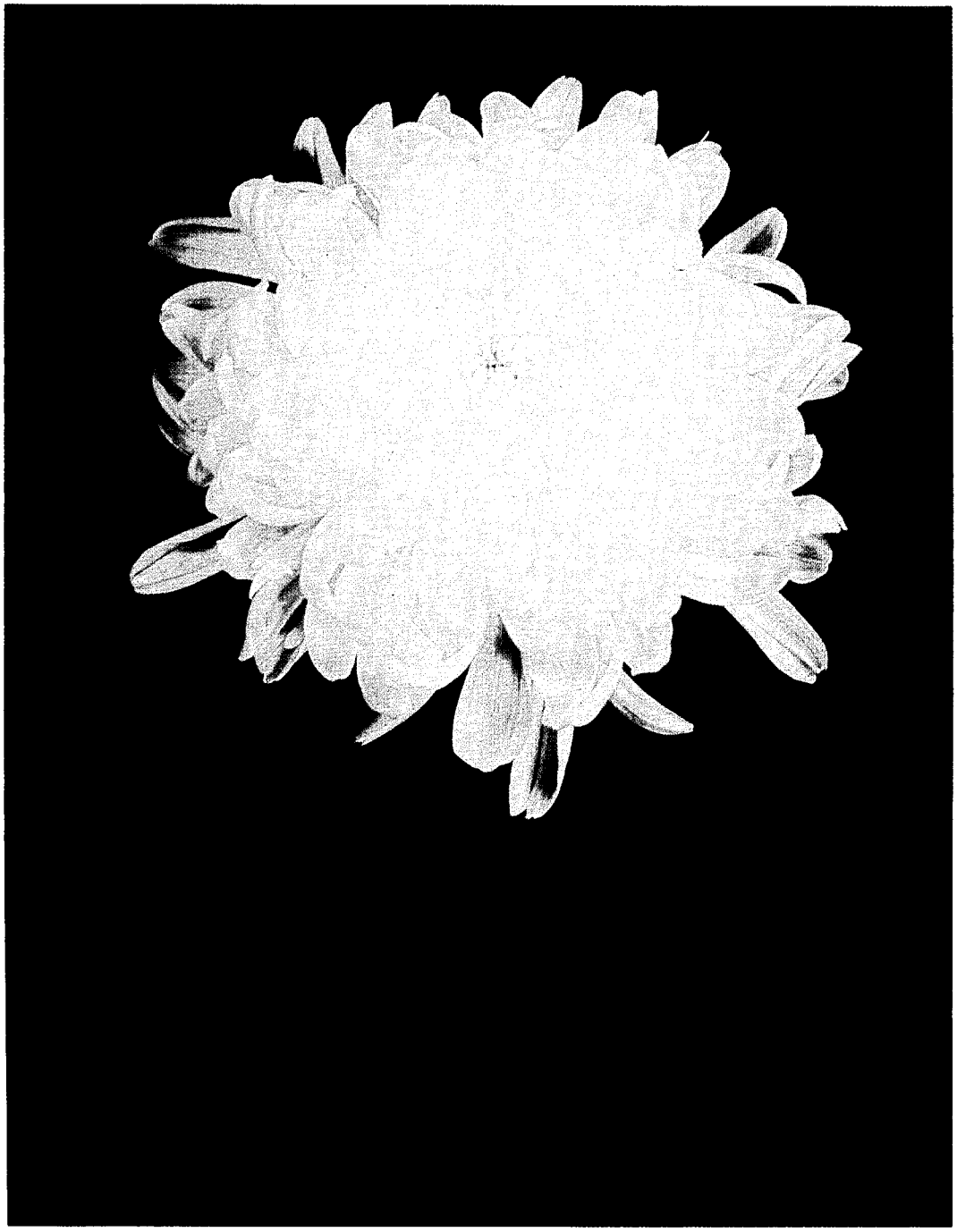

United States Patent Office

Plant Pat. 3,657
Patented Nov. 26, 1974

3,657

CHRYSANTHEMUM PLANT

Walter H. Jessel, Jr., Doylestown, and William E. Duffett, Akron, Ohio, assignors to Yoder Brothers, Inc., Barberton, Ohio

Filed Oct. 10, 1973, Ser. No. 404,982
Int. Cl. A01h *5/00*
U.S. Cl. Plt.—78 1 Claim

The present invention comprises a new and distinct cultivar of chrysanthemum plant known by the varietal name Yellow Sea Foam which is a sport of the seedling known by the varietal name Sea Foam, which is disclosed in our copending application Ser. No. 404,983, filed Oct. 10, 1973.

Like its parent, the new cultivar is a winter standard but is distinguished therefrom by its yellow flower color, as contrasted to the ivory white flower color of Sea Foam. The new cultivar is also distinguished from the parent variety by its approximately 2–3″ less vigor, approximately 1–2 days later response, ½″ smaller flower size, and by its foliage which is lighter in color and ½″ smaller in length and width.

The new cultivar can also be compared to Goldburst Mefo and Improved Rivalry, both of which are yellow winter standards well known in the floriculture industry. With respect to these varieties, the new cultivar has a less intense yellow flower color, a substantially earlier response period (approximately nine weeks) and a somewhat smaller flower size, ranging from 5¼″ to 5¾″ when fully expanded.

The primary characteristics of the new variety are as follows:

1. A pleasant, less intense yellow flower color.
2. An early, nine week response.
3. Superior form retention and vigor.
4. A flower size which ranges from 5¼″ to 5¾″ when fully expanded.
5. A light, medium green foliage having moderately indented edges.
6. A tolerance of marginal temperature for uniform bud initiation and development down to 56° F.

Yellow Sea Foam was selected from a flowering block of the parent variety Sea Foam. The Sea Foam cuttings were previously exposed to 1800 roentgens of X-radiation. First asexual reproduction by vegetative cuttings of Yellow Sea Foam was accomplished by us in August 1971 in a greenhouse in Barberton, Ohio. Continued asexual reproduction has demonstrated that Yellow Sea Foam retains its distinctive characteristics through successive generations.

The new cultivar when grown in the vicinity of Barberton, Ohio, has a response period of approximately nine weeks, and the following detailed description is based on observations made of the new cultivar in a greenhouse in Barberton, Ohio. The response time, blooming period, color, and total vigor may very significantly with varying environmental conditions such as temperature, daylength, and light intensity. Suggested flowering in the northern and western United States is from October through May; southeastern and southwestern United States, November through mid-April; coastal California, November through mid-September; and Florida, December through March 15.

The accompanying photographic drawing shows the unique charateristics of the new cultivar with the color being as nearly true as possible with color illustrations of this type. In the description which follows, color references are made to the Munsell Color Notation.

Botanical Classification: Chrysanthemum morifolium.

*Yellow Sea Foam*

Bloom:
- *Size.*—5¼″.
- *Fully expanded.*—5¾″.
- *Borne.*—Singly on disbudded plants.
- *Stems.*—Strong and heavy.
- *Form.*—Semi-incurve.
- *Permanence.*—10–14 days.
- *Color.*—Center of flower—yellow, 6.25Y8.5/12. Base of petals—light yellow-green, 2.5GY7/8. Inside of petals—yellow, 6.6Y8.6/11.4 to light yellow, 0.6GY9/7.8. Reverse of petals—light yellow, 0.6GY9/7.8 to pale yellow, 7.8Y9/4. Tonality from a distance—yellow. Discoloration—light yellow, 0.6GY9/7.8.

Petals:
- *Texture.*—Smooth.
- *Appearance and form.*—Closed at base, opening slowly with a pronounced inward marginal roll. Smooth rounded keel tapering to a blunt semi-hooded tip.
- *Arrangement.*—Composite, whorled on a single receptacle.
- *Persistence.*—Resists shatter.
- *Fragrance.*—Typical chrysanthemum.

Reproductive organs:
- *Stamen, anthers.*—5–20.
- *Pollen.*—Scant.
- *Arrangement.*—Clustered in center of flower, if present.
- *Styles.*—Present both ray and disc florets.
- *Length.*—Short.
- *Ovaries.*—At the base of petal attached to receptacle.

Plant:
- *Form.*—Herbaceous.
- *Growth.*—Upright.
- *Height.*—Approximately 36″–40″ given 2–5 long day weeks and 11–14 weeks total crop time as defined in the timetables of Yoder Brothers, Inc., Barberton, Ohio, for the various seasons.
- *Spread.*—None grown single stem to slight when pinched.

Foliage:
- *Top side.*—Medium green, 7.5GY4/4.
- *Size.*—Length to width ratio 29:20 with length to 7¼″ and width to 5″.
- *Quantity.*—Numerous.
- *Shape.*—Spatulate lobed.
- *Texture.*—Smooth.
- *Ribs and veins.*—Moderately prominent.
- *Edge.*—Moderately indented.
- *Serration.*—Coarse.
- *Under side.*—Greyed medium green, 7.5GY5/4.
- *Stipules.*—Very prominent.

We claim:

A new and distinct cultivar of chrysanthemum characterized particularly by its less intense yellow flower color, a nine week response period, superior vigor and form retention, a flower size which ranges from 5¼″ to 5¾″ when expanded, a light, medium green foliage having moderately indented edges, and by its excellent tolerance of marginal temperatures for uniform bud initiation and development.

No references cited.

ROBERT E. BAGWILL, Primary Examiner